United States Patent

Yamamoto et al.

[11] Patent Number: 6,121,326
[45] Date of Patent: Sep. 19, 2000

[54] SUBSTITUTED ALKYLTETRAAMINE DERIVATIVES

[75] Inventors: Atsushi Yamamoto; Ko Nakamura; Masanori Otsuka, all of Hyogo, Japan

[73] Assignee: Nippon Zoki Pharmaceutical Co., Ltd., Osaka, Japan

[21] Appl. No.: 09/477,824

[22] Filed: Jan. 5, 2000

[51] Int. Cl.$^7$ ...................................................... A01N 37/18
[52] U.S. Cl. ........................ 514/616; 514/617; 564/134; 564/139; 564/142; 564/144; 564/153; 564/155; 564/158
[58] Field of Search ..................... 564/139, 134, 564/142, 144, 153, 155, 158; 514/616, 617

[56] References Cited

U.S. PATENT DOCUMENTS 5,218,000  6/1993  Usherwood et al. .................... 514/617

OTHER PUBLICATIONS

Jentgens et al, "Selective Synthesis of Polyamine Derivatives: Efficient Derivitazation of the Secondary Amino Group of N–Monosubstituted 1,3–Diamines", Helvetica Chimica Acta, vol. 80, pp. 966–978, Dec. 1997.

Martin–Tanguy et al, "The Distribution of Hydroxycinnamic Acid Amides in Flowering Plants", Phytochemistry 17:11, p. 1927–8, Dec. 1978.

Primary Examiner—Frederick Krass
Attorney, Agent, or Firm—Hollander Law Firm, P.L.C.

[57] ABSTRACT

Compounds which are useful as a tachykinin antagonist are substituted alkyltetraamine derivatives which are represented by the following formula (I) or a pharmaceutically acceptable salt, a complex compound or a solvate thereof.

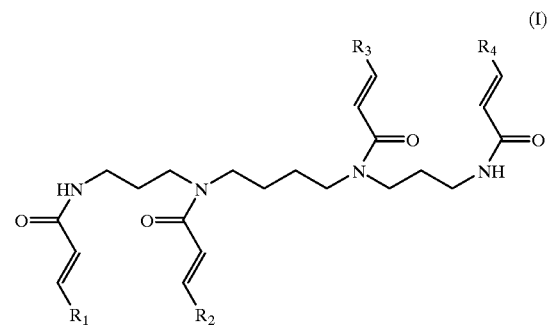

wherein $R_1$, $R_2$, $R_3$ and $R_4$ are the same or different and each is a phenyl group which may be substituted with one or more hydroxyl, lower alkoxy and/or acyloxy group(s). The compounds are useful as an anti-inflammatory agent, antiallergic agent, analgesic, antiemetic, agent for irritable colon syndrome, agent for dermal disease, agent for vasospastic disease, agent for cerebral ischemic disease, antidepressant, antianxiety agent, agent for autoimmune disease, antispasmodic, and as a muscle relaxant, etc.

22 Claims, No Drawings

SUBSTITUTED ALKYLTETRAAMINE DERIVATIVES

FIELD OF THE INVENTION

The present invention relates to substituted alkyltetraamine derivatives which are useful as a tachykinin antagonist.

BACKGROUND OF THE INVENTION

Tachykinin is a general term for a group of peptides having similar structures. Substance P (SP), neurokinin A (NKA) and neurokinin B (NKB) are representative of tachykinins in mammals. The tachykinins are neuro-peptides widely distributed in the living body, with substance P being the most fully investigated for physiological functions among them. Substance P is a peptide consisting of 11 amino acids and has been known to exhibit hypotensive action, smooth muscle constricting action, sialagogue action, neuron exciting action, pain inducing action, etc.

Substance P has been known to act in broad areas such as in diseases of the digestive system, nervous system and respiratory system. It is believed to be especially deeply associated with inflammation, allergy, carcinoid syndrome, chronic pain, headache, Crohn disease, depression and vomiting. Accordingly, a tachykinin antagonist is applicable to many diseases and is useful as an anti-inflammatory agent, anti-allergic agent, analgesic, antiemetic, agent for irritable colon syndrome, agent for dermal disease, agent for vasospastic disease, agent for cerebral ischemic disease, antidepressant, antianxiety agent, agent for autoimmune disease, and as a muscle relaxant or antispasmodic. Various tachykinin antagonists have been developed and reported with an object of development of therapeutic agents for those diseases in which tachykinins participate.

Several tachykinin receptor antagonists have been reported. Most of them reported in 1980 were developed by derivation from intrinsic tachykinin of mammals. Namely, a portion of the amino acids constituting the intrinsic tachykinin was substituted with a D-amino acid or the like. However, they are peptides, and accordingly preferred pharmacokinetic properties are not achieved, and there is a limit for expression of activity in vivo. To overcome such a disadvantage, tachykinin receptor antagonists which are non-peptide types are now being developed although none of them have been commercialized as a pharmaceutical agent.

The present invention provides a tachykinin antagonist having a novel chemical structure. The structure of the present compounds is entirely different from the tachykinin receptor antagonists of the non-peptide type which have already been developed.

The present inventors have carried out an intensive investigation involving substituted alkyltetraamine compounds extracted and purified from *Matricaria chamomilla* which is a plant belonging to the family Compositae, and have prepared derivatives thereof. As a result, they have found that those compounds have a tachykinin antagonistic action and accomplished the present invention.

SUMMARY OF THE INVENTION

Compounds which are useful as a tachykinin antagonist are substituted alkyltetraamine derivatives which are represented by the following formula (I) or a pharmaceutically acceptable salt, a complex compound or a solvate of the substituted alkyltetraamine derivatives which are represented by formula (I):

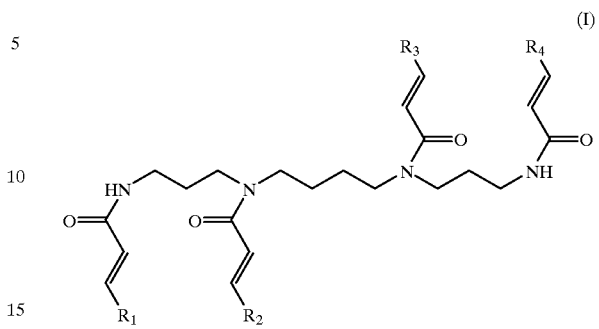

wherein $R_1$, $R_2$, $R_3$ and $R_4$ are the same or different and each of $R_1$, $R_2$, $R_3$ and $R_4$ is a phenyl group, or a phenyl group which is substituted with at least one member selected from the group consisting of hydroxyl, lower alkoxy and acyloxy groups.

The compounds may be produced by reacting spermine represented by the formula (II) or a reactive derivative thereof, with a carboxylic acid of formula (III) or a reactive derivative thereof:

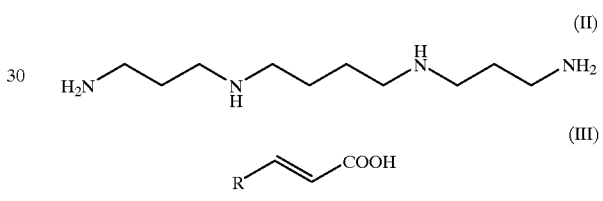

wherein R is a group corresponding to $R_1$, $R_2$, $R_3$ and $R_4$ in the formula (I).

In embodiments of the invention, compounds of formula (I) may be obtained by isolation or purification from an extract of a plant belonging to the family Compositae, such as *M. chamomilla*.

The substituted alkyltetraamine derivatives of the present invention are useful as an anti-inflammatory agent, anti-allergic agent, analgesic, antiemetic, agent for irritable colon syndrome, agent for dermal disease, agent for vasospastic disease, agent for cerebral ischemic disease, antidepressant, antianxiety agent, agent for autoimmune disease, antispasmodic, and as a muscle relaxant, etc.

Pharmaceutical compositions comprising a pharmaceutically effective amount of at least one compound of the present invention may be used for the treatment of a tachykinin-related disease or condition such as anxiety, depression, schizophrenia, senile pollakiuria, incontinence, Crohn disease, irritable colon syndrome, inflammatory intestinal disease, chronic articular rheumatism, vomiting, migraine, pain, ulcer, asthma, allergic disease, ocular disease, dermal disease, inflammatory disease, and diabetic neuropathy.

DETAILED DESCRIPTION OF THE INVENTION

The present invention provides a compound represented by the following formula (I) or a pharmaceutically acceptable salt, a complex compound or a solvate thereof and also relates to a tachykinin antagonist containing the compound as an effective ingredient:

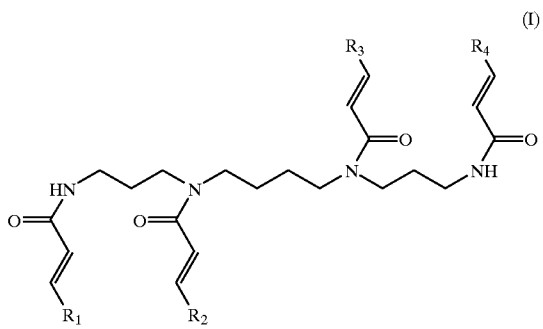

(I)

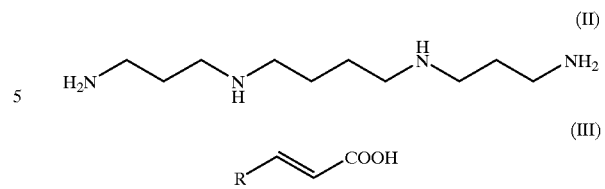

(II)

(III)

wherein R is a group corresponding to $R_1$, $R_2$, $R_3$ and $R_4$ in the formula (I).

When the carboxylic acid of the formula (III) is made to react in a free acid form, it is preferred to conduct the reaction using an appropriate organic solvent in the presence of a coupling reagent. Examples of the coupling reagent which may be employed are 1,1-carbonyldiimidazole, 1-ethoxy-carbonyl-2-ethoxy-1,2-dihydroxyquinoline, N,N dicyclohexylcarbodiimide and diphenylphosphoryl azide.

As a reactive derivative of the carboxylic acid, an acid halide such as an acid chloride or acid bromide, an acid azide, an active ester of 1-hydroxybenzotriazole or N-hydroxysuccinimide, an acid anhydride of the symmetric type, an alkyl carbonate mixed acid anhydride, a p-toluenesulfonic acid mixed acid anhydride, and the like may be employed.

In the synthesis reaction, the compound (II) or a reactive derivative thereof and the compound (III) may be used in a substantially equimolar amount, or one of them may be used in an excessive amount. Both compounds may be reacted in an inert organic solvent which does not affect the reaction such as tetrahydrofuran, dioxane, benzene, methylene chloride, dichloroethane, chloroform, ethyl acetate, acetonitrile, dimethylformamide, dimethyl sulfoxide or pyridine.

According to the type of the reactive derivative, it may be advantageous for carrying out the reaction in a smooth manner to add a base such as N-methylmorpholine, triethylamine, pyridine, lutidine, N,N-dimethylaniline, potassium carbonate or sodium hydroxide to the reaction mixture.

The reaction temperature may vary depending upon the type of the reactive derivative and so can be appropriately set. In embodiments of the invention, a synthesis involving a spermine of formula (II) and an acid halide derivative of an acid of formula (III) may be conducted at about room temperature and atmospheric pressure in about 12 to 16 hours.

When the substituent $R_1$, $R_2$, $R_3$ and $R_4$ are different in the compound of formula (I), the synthesis may be performed from an intermediate thereof where a protective group is introduced to any of the amino groups. Alternatively, it is possible to utilize a transferase such as spermine hydroxycinnamoyl transferase.

For isolation and purification of the objective product, such as a compound of formula (I), from the reaction mixture, conventional means such as extraction with solvent, concentration, recrystallization and chromatography may be appropriately used.

One of the compounds of the present invention (Compound 2 in Example 1) may be extracted and isolated from plants of the family Compositae such as *Matricaria chamomilla* and *Carthamus tinctorius*. A conventional method for extraction from plant materials may be utilized. For example, an extraction method using an extracting solvent such as an organic solvent (e.g., methanol, ethanol or acetone) or an aqueous organic solvent may be employed. For isolation of the target compound from the extract, a wherein, $R_1$, $R_2$, $R_3$ and $R_4$ are the same or different and each of them is a phenyl group which may be substituted with one or more hydroxyl, lower alkoxy and/or acyloxy group(s).

In formula (I), "lower alkoxy" preferably represents a linear or branched alkoxy having 1 to 6 carbon atoms such as methoxy, ethoxy, propoxy, isopropoxy, butoxy, isobutoxy, sec-butoxy or t-butoxy, pentyloxy, isopentyloxy, neopentyloxy, t-pentyloxy, hexyloxy, isohexyloxy or dimethylbutoxy. Also, as an acyl group of the "acyloxy" group, a linear or branched acyl having 1 to 4 carbon atoms such as formyl, acetyl, propionyl, butyryl, isobutyryl or t-butyryl, or benzoyl is preferred.

The compounds of the present invention include pharmaceutically acceptable salts of the compounds represented by the above formula (I). Also, when there are stereo-isomers such as a cis-trans isomer, optical isomer and conformational isomer, or complex compounds thereof, the present invention includes such isomers and complex compounds. Further, the present invention includes a solvate of the compounds represented by the formula (I) with water, methanol, ethanol or acetonitrile, namely, a pharmaceutically acceptable solvate such as hydrate, methanolate, ethanolate or acetonitrate.

Preferred embodiments of the present invention are:

(1) A substituted alkyltetraamine derivative represented by the above formula (I) or a pharmaceutically acceptable salt, a complex compound or a solvate thereof.

(2) The substituted alkyltetraamine derivative according to paragraph (1) wherein $R_1$, $R_2$, $R_3$ and $R_4$ are the same substituent.

(3) The substituted alkyltetraamine derivative according to paragraph (2) wherein $R_1$, $R_2$, $R_3$ and $R_4$ are phenyl substituted with one hydroxyl.

(4) The substituted alkyltetraamine derivative according to paragraph (3) wherein $R_1$, $R_2$, $R_3$ and $R_4$ are 4-hydroxyphenyl.

(5) A pharmaceutical composition containing a substituted alkyltetraamine derivative according to any one of paragraphs (1) to (4) as an effective ingredient.

(6) The pharmaceutical composition according to paragraph (5), wherein the composition is a tachykinin antagonist.

The compound represented by the formula (I) may be manufactured employing reactants represented by the formulae (II) and (III). The synthesis includes an acid amide reaction of spermine represented by the formula (II) or a reactive derivative thereof, with a carboxylic acid of formula (III) or a reactive derivative thereof:

purification method frequently used in this field may be utilized. For example, chromatography such as silica gel chromatography or HPLC may be used for isolation and purification of the compound of the present invention. The compounds may be identified by means of, for example, elementary analysis, melting point measurement, infrared (IR), nuclear magnetic resonance (NMR), ultraviolet (UV), and mass spectroscopy (MS).

The compounds of the present invention, which include the substituted alkyltetraamine derivatives represented by the formula (I) and pharmaceutically acceptable salts, complexes, and solvates of the derivatives represented by the formula (I), can be made into pharmaceutical preparations by combining one or more of the compounds with at least one pharmaceutically acceptable carrier or diluent. They can be made into various types of preparations by known methods. The compounds of the invention can be made into solid, semisolid, liquid or aerosol formulations for administration by oral or parenteral means. Any of the known methods for providing preparations, such as for oral administrations (e.g. tablets, capsules, powders, liquids, etc.) and for parenteral administrations (e.g. for subcutaneous, intravenous, intramuscular, intrarectal and intranasal administrations) may be used to produce the pharmaceutical compositions of the present invention.

The compounds of the present invention may be used either solely or jointly in pharmaceutically effective amounts for treating animals or humans. The compounds of the invention can be used either solely or jointly together in pharmaceutically acceptable amounts with pharmaceutically effective amounts of other pharmaceutically active components in pharmaceutical compositions or preparations.

In the case of preparations for oral administration, one or more of the compounds of the present invention either alone or in combination with commonly-used pharmaceutically acceptable excipients in pharmaceutically acceptable amounts such as at least one suitable pharmaceutically acceptable additive or carrier (e.g. lactose, mannitol, corn starch, potato starch, etc.) may be mixed with one or more pharmaceutically acceptable: (1) binders such as cellulose, crystalline cellulose, gum arabicum, corn starch, gelatin, etc., (2) disintegrating agents such as corn starch, potato starch, potassium carboxymethylcellulose, etc., (3) lubricating agents such as talc, magnesium stearate, etc. and (4) other pharmaceutically acceptable excipients including pharmaceutically acceptable bulking agents, moisturizing agents, buffers, preservatives, perfumes and the like to obtain tablets, diluted powders, granules or capsules.

Alternatively, suppositories may be prepared by mixing at least one compound of the present invention with pharmaceutically acceptable amounts of one or more pharmaceutically acceptable fatty/oily bases (e.g. cacao butter), emulsified bases, water-soluble bases (e.g. Macrogol), hydrophilic bases, etc.

In the case of injections, it is possible to prepare solutions or suspensions of one or more compounds of the present invention in pharmaceutically acceptable carriers such as an aqueous or nonaqueous solvent. Examples of solvents which may be used are distilled water for injection, physiological saline solution, Ringer's solution, plant oil, synthetic fatty acid glycerides, higher fatty acid esters, propylene glycol, etc.

In the case of inhalations or aerosol preparations, at least one compound of the present invention in the form of a liquid or fine powder can be filled up in an aerosol container with a gas or liquid spraying agent, and if desired, with conventional adjuvants such as one or more pharmaceutically acceptable humidifying agents or dispersing agents. They can also be used as pharmaceuticals for a non-pressurized preparation such as in a nebulizer or an atomizer.

It is also possible, depending upon the type of the disease, to prepare pharmaceutical preparations other than the above-mentioned ones which are suitable for therapy depending upon the type of disease. Exemplary of other pharmaceutical preparations are collyriums, ointments, cataplasms, etc.

The preferred dosage of the compound of the present invention varies depending upon the subject to be administered (age, body weight, symptoms, etc. of the patient), form of the preparation, method for the administration, term for the administration, etc. To achieve the desired result, the compound may be usually administered by the oral route with a daily dose of 0.01–100 mg per day, preferably 0.05–25 mg per day, to common adults either once daily or several times a day.

In the case of a parenteral administration such as by injection, the preferred dosage may be from $1/3$ to $1/10$ of the above-mentioned oral dosages because of the effects of absorption, etc. in the oral route.

The present invention is illustrated by the following examples wherein all parts, percentages and ratios are by weight, all temperatures are in ° C., and all reactions are conducted at about atmospheric pressure unless indicated to the contrary:

EXAMPLE 1

In this example, 3-(4-acetoxyphenyl)-2-propenoic acid, a compound of formula (III), is produced and then converted to its acid chloride. The acid chloride is reacted with spermine of formula (II) to obtain N1,N5, N10,N14-tetrakis [3-(4-acetoxyphenyl)-2-propenoyl]tetraazatetradecane, a compound of formula (I). The latter compound is then reacted to obtain N1,N5,N10,N14 -tetrakis[3-(4-hydroxyphenyl)-2-propenoyl]tetraazatetradecane which is another compound of formula (I):

1) 3-(4-Acetoxyphenyl)-2-propenoic acid

In 40 ml of pyridine were dissolved 3.28 g (20 mmol) of 3-(4-hydroxyphenyl)-2-propenoic acid, then 6.5 ml of acetic anhydride were added thereto and the mixture was stirred overnight at room temperature. The reaction mixture was evaporated to dryness in vacuo and 150 ml of ethyl acetate and 150 ml of 1M hydrochloric acid was added thereto followed by mixing. The organic phase was dried over sodium sulfate and the solvent was evaporated therefrom in vacuo. Ether was added to the residue to crystallize 3-(4-acetoxyphenyl)-2-propenoic acid whereupon 3.79 g (yield: 92%) of the 3-(4-acetoxyphenyl)-2-propenoic acid were obtained.

2) 3-(4-Acetoxyphenyl)-2-propenoyl chloride

In 100 ml of dichloromethane were dissolved 3.79 g (19.4 mmol) of 3-(4-acetoxyphenyl)-2-propenoic acid, then 4.8 ml (67 mmol) of thionyl chloride were added thereto and the mixture was stirred at room temperature for 3 hours. The reaction mixture was evaporated to dryness in vacuo and ether-hexane (1/1) was added to the residue to crystallize 3-(4-Acetoxyphenyl)-2-propenoyl chloride whereupon 2.89 g (yield: 70%) of the 3-(4-acetoxyphenyl)-2-propenoyl chloride were obtained.

3) N1,N5,N10,N14-Tetrakis[3-(4-acetoxyphenyl)-2-propenoyl]tetraazatetradecane (Compound 1)

To 80 ml of tetrahydrofuran in which 1.01 g (5 mmol) of spermine and 2.12 g (21 mmol) of triethylamine were dissolved were added 4.70 g (21 mmol) of 3-(4-acetoxyphenyl)-2-propenoyl chloride and the mixture was stirred overnight at room temperature. To the reaction solution 10-fold by volume of water was added, the solvent was filtered off and the residue was washed with water to give 3.96 g (yield: 83%) of N1,N5,N10,N14-tetrakis[3-(4-acetoxyphenyl)-2-propenoyl]tetraazatetradecane (Compound 1) as a white powder.

$^1$H–NMR (δ, DMSO): 1.49–1.62 (m, 4H), 1.70–1.81 (m, 4H), 2.24 (s, 3H), 2.25 (s, 3H), 2.27 (Br, s, 6H), 3.14–3.54 (m, 12H), 6.57–6.63 (m, 2H), 7.00–7.06 (m, 4H), 7.09–7.18 (m, 6H), 7.40–7.53 (m, 4H), 7.57–7.62 (m, 4H), 7.64–7.79 (m, 4H), 8.09–8.14 (m, 1H), 8.21–8.26 (m, 1H).

4) N1,N5,N10,N14-Tetrakis[3-(4-hydroxyphenyl)-2-propenoyl]tetraazatetradecane (Compound 2)

To 954 mg of N1,N5,N10,N14-tetrakis[3-(4-acetoxyphenyl)-2-propenoyl]tetraazatetradecane were added 4.8 equivalents of 1M sodium hydroxide and the mixture was allowed to stand at room temperature for 1 hour. After this was neutralized with 4.8 equivalents of 1M hydrochloric acid, an excessive amount of water was added thereto and the resulting precipitate was washed with water to give 676 mg (yield 86%) of N1,N5,N10,N14-tetrakis[3-(4-hydroxyphenyl)-2-propenoyl]tetraazatetradecane (Compound 2) as a white powder.

$^1$H–NMR (δ, DMSO): 1.45–1.80 (m, 8H), 3.12–3.55 (m, 12H), 6.36–6.44 (m, 2H), 6.68–6.94 (m, 10H), 7.29–7.56 (m, 12H), 7.94–7.98 (m, 1H), 8.05–8.11 (m, 1H), 9.69–9.92 (m, 4H).

EXAMPLE 2

In this example, 3-(4-acetoxy-3-methoxyphenyl)-2-propenoic acid, a compound of formula (III), is produced and then converted to its acid chloride. The acid chloride is reacted with spermine of formula (II) to obtain N1,N5,N10, N14-tetrakis[3-(4-acetoxy-3-methoxyphenyl)-2-propenoyl] tetraazatetradecane, a compound of formula (I). The latter compound is then reacted to obtain N1,N5,N10,N14-tetrakis [3-(4-hydroxy-3-methoxyphenyl)-2-propenoyl] tetraazatetradecane, which is another compound of formula (I):

1) 3-(4-Acetoxy-3-methoxyphenyl)-2-propenoic acid

In 80 ml of pyridine were dissolved 7.77 g (40 mmol) of 3-(4-hydroxy-3-methoxyphenyl)-2-propenoic acid, then 12 ml of acetic anhydride were added thereto and the mixture was stirred overnight at room temperature. The reaction mixture was evaporated to dryness in vacuo and 400 ml of ethyl acetate and 400 ml of 1M hydrochloric acid were added thereto followed by mixing. The organic phase was dried over sodium sulfate and the solvent was evaporated therefrom in vacuo. Ether was added to the residue to crystallize 3-(4-Acetoxy-3-methoxyphenyl)-2-propenoic acid whereupon 8.71 g (yield: 92%) of the 3-(4-Acetoxy-3-methoxyphenyl)-2-propenoic acid were obtained.

2) 3-(4-Acetoxy-3-methoxyphenyl)-2-propenoyl chloride

In 80 ml of dichloromethane were dissolved 4.72 g (20 mmol) of 3-(4-acetoxy-3-methoxyphenyl)-2-propenoic acid, then 5.2 ml of thionyl chloride were added thereto and the mixture was stirred at room temperature for 15 hours. The reaction mixture was evaporated to dryness in vacuo and ether-hexane (1/1) was added to the residue to crystallize 3-(4-acetoxy-3-methoxyphenyl)-2-propenoyl chloride whereupon 4.27 g (yield: 84%) of the 3-(4-acetoxy-3-methoxyphenyl)-2-propenoyl chloride were obtained.

3) N1,N5,N10,N14-Tetrakis[3-(4-acetoxy-3-methoxyphenyl)-2-propenoyl]tetraazatetradecane (Compound 3)

To 50 ml of tetrahydrofuran in which 404 mg (2 mmol) of spermine and 850 mg (8.4 mmol) of triethylamine were dissolved were added 2.13 g (8.4 mmol) of 3-(4-acetoxy-3-methoxyphenyl)-2-propenoyl chloride and the mixture was stirred overnight at room temperature. The solvent was filtered, the filtrate was evaporated to dryness in vacuo and the residue was dissolved in 10 ml of chloroform. Purification was carried out by means of a chromatographic treatment on silica gel using a mixture of 4% methanol and 96% chloroform as an eluent whereupon 1.88 g (yield: 88%) of N1,N5,N10,N14-tetrakis[3-(4-acetoxy-3-methoxyphenyl)-2-propenoyl]tetraazatetradecane (Compound 3) were obtained as a white powder.

$^1$H–NMR (δ, DMSO): 1.52–1.64 (m, 4H), 1.69–1.80 (m, 4H), 2.23–2.27 (m, 12H), 3.16–3.59 (m, 12H), 3.78–3.82 (m, 12H), 6.58–6.65 (m, 2H), 6.93–7.52 (m, 18H), 8.08–8.13 (m, 1H), 8.17–8.22 (m, 1H).

4) N1,N5,N10,N14-Tetrakis[3-(4-hydroxy-3-methoxyphenyl)-2-propenoyl]tetraazatetradecane (Compound 4)

In 20 ml of methanol were dissolved 1.07 g of N1,N5, N10,N14-tetrakis[3-(4-acetoxy-3-methoxyphenyl)-2-propenoyl]tetraazatetradecane, 4.8 equivalents of 1M sodium hydroxide were added thereto and the mixture was allowed to stand at room temperature for 1 hour. After this was neutralized with 4.8 equivalents of 1M hydrochloric acid, an excessive amount of water was added thereto and the resulting precipitate was washed with water to give 0.834 g (yield 92%) of N1,N5,N10,N14-tetrakis[3-(4-hydroxy-3-methoxyphenyl)-2-propenoyl] tetraazatetradecane (Compound 4) as a pale yellow powder.

$^1$H–NMR (δ, DMSO): 1.46–1.76 (m, 8H), 3.16–3.49 (m, 12H), 6.30–6.36 (m, 2H), 6.68–6.85 (m, 8H), 6.92–7.10 (m, 6H), 7.21–7.35 (m, 4H), 7.98–8.01 (m, 1H), 8.06–8.09 (m, 1H), 8.91–9.54 (Br, m, 8H).

EXAMPLE 3

In this example, 3-(3,4-diacetoxyphenyl)-2-propenoic acid, a compound of formula (III), is produced and then converted to its acid chloride. The acid chloride is reacted with spermine of formula (II) to obtain N1,N5,N10,N14-tetrakis[3-(3,4-diacetoxyphenyl)-2-propenoyl] tetraazatetradecane, a compound of formula (I). The latter compound is then reacted to obtain N1,N5,N10,N14-tetrakis [3-(3,4-dihydroxyphenyl)-2-propenoyl]tetraazatetradecane which is another compound of formula (I):

1) 3-(3,4-Diacetoxyphenyl)-2-propenoic acid

In 80 ml of pyridine were dissolved 7.21 g (40 mmol) of 3-(3,4-dihydroxyphenyl)-2-propenoic acid, then 24 ml of acetic anhydride were added thereto and the mixture was stirred overnight at room temperature. The reaction mixture was evaporated to dryness in vacuo and 200 ml of ethyl acetate and 200 ml of 1M hydrochloric acid were added thereto followed by mixing. The organic phase was dried over sodium sulfate and the solvent was evaporated therefrom in vacuo. Ether was added to the residue to crystallize 3-(3,4-diacetoxyphenyl)-2-propenoic acid whereupon 8.89 g (yield: 84%) of the 3-(3,4-diacetoxyphenyl)-2-propenoic acid were obtained.

2) 3-(3,4-Diacetoxyphenyl)-2-propenoyl chloride

In 150 ml of dichloromethane were dissolved 8.89 g (33.67 mmol) of 3-(3,4-diacetoxyphenyl)-2-propenoic acid, then 8.8 ml of thionyl chloride were added thereto and the mixture was stirred at room temperature for 6 hours. The reaction mixture was evaporated to dryness in vacuo and ether-hexane (1/1) was added to the residue to crystallize 3-(3,4-diacetoxyphenyl)-2-propenoyl chloride whereupon 7.90 g (yield: 83%) of the 3-(3,4-diacetoxyphenyl)-2-propenoyl chloride were obtained.

3) N1,N5,N10,N14-Tetrakis[3-(3,4-diacetoxyphenyl)-2-propenoyl]tetraazatetradecane (Compound 5)

To 50 ml of tetrahydrofuran in which 404 mg (2 mmol) of spermine and 850 mg (8.4 mmol) of triethylamine were dissolved were added 2.37 g (8.4 mmol) of 3-(3,4-diacetoxyphenyl)-2-propenoyl chloride and the mixture was stirred overnight at room temperature. The solvent was filtered, the filtrate was evaporated to dryness in vacuo, the residue was dissolved in 10 ml of chloroform and purification was carried out by means of a chromatographic treatment on silica gel using a mixture of 4% methanol and 96% chloroform as an eluent whereupon 2.06 g (yield: 87%) of N1,N5,N10,N14-tetrakis[3-(3,4-diacetoxyphenyl)-2-propenoyl]tetraazatetradecane (Compound 5) were obtained as a white powder.

$^1$H–NMR ($\delta$, DMSO): 1.48–1.60 (m, 4H), 1.66–1.79 (m, 4H), 2.26–2.31 (m, 24H), 3.16–3.54 (m, 12H), 6.56–6.63 (m, 2H), 7.07–7.66 (m, 18H), 8.08–8.13 (m, 1H), 8.16–8.22 (m, 1H).

4) N1,N5,N10,N14-Tetrakis[3-(3,4-dihydroxyphenyl)-2-propenoyl]tetraazatetradecane (Compound 6)

In 40 ml of methanol were dissolved 2.06 g of N1,N5,N10,N14-tetrakis[3-(3,4-diacetoxyphenyl)-2-propenoyl]tetraazatetradecane, 9.6 equivalents of 1M sodium hydroxide were added thereto and the mixture was allowed to stand at room temperature for 1 hour. After this was neutralized with 4.8 equivalents of 1M hydrochloric acid, an excessive amount of water was added thereto and the resulting precipitate was recovered and washed with water to give 0.926 g (yield 74%) of N1,N5,N10,N14-tetrakis[3-(3,4-dihydroxyphenyl)-2-propenoyl]tetraazatetradecane (Compound 6) as a pale brown powder.

$^1$H–NMR ($\delta$, DMSO): 1.49–1.76 (m, 8H), 3.16–3.53 (m, 12H), 3.77–3.81 (m, 12H), 6.24–6.46 (m, 2H), 6.70–7.43 (m, 18H), 7.66–7.98 (m, 1H), 7.99–8.02 (m, 1H), 9.47 (s, 4H).

EXAMPLE 4

Pharmacological Test: Tachykinin Antagonistic Action

The compounds of the present invention were tested by an assay using ileum isolated from guinea pigs. Male guinea pigs of the Hartley strain (400 g to 500 g) were fainted and bled out. Then, ileum was isolated and hung in an organ bath filled with a nutritive solution. After an equilibration for 60 minutes, isotonic contraction was recorded. Substance P, a tachykinin agonist, was administered in a dose of $10^{-8}$M every 15 minutes. Administration of substance P was repeated for 3 to 4 times and it was confirmed that a contraction height for each run became constant. The constant contraction was used as a control. A treatment with the test drug was carried out for 10 minutes and then substance P was administered again and a concentration vs. action curve was prepared. A 50% suppression concentration ($IC_{50}$) was determined from the concentration vs. action curve of the test drug. The compound of the present invention was used as a test drug and an example of the result of its antagonistic action to substance P is shown in Table 1:

TABLE 1

| Compound No. tested | Antagonistic action to Substance P $IC_{50}$ ($\mu$M) |
|---|---|
| 1 | 0.014 |
| 2 | 0.011 |
| 3 | 0.71 |
| 4 | 0.58 |

It is apparent from the results of the above-mentioned pharmacological tests that the compounds of the present invention have an antagonistic action to tachykinins such as substance P and neurokinin A. Accordingly, they are useful for treatment or prevention of tachykinin-related diseases such as anxiety, depression, schizophrenia, asthma, senile pollakiuria, incontinence, Crohn disease, irritable colon syndrome, inflammatory intestinal disease, chronic articular rheumatism, vomiting, vomiting due to anticancer agents, migraine, pain, ulcer, diseases of respiratory system such as chronic bronchitis ocular diseases such as conjunctivitis, dermal diseases such as contact dermatitis, atopic dermatitis, urticaria and other eczematous dermatitis, inflammatory disease and diabetic neuropathy.

The compounds of the present invention include the novel compound N1,N5,N10,N14-tetrakis[3-(4-hydroxyphenyl)-2-propenoyl]tetraazatetradecane (Compound 2) which was isolated and purified from an extract of *Matricaria chamomilla* which is a plant belonging to the family Compositae, and synthetic analogous new compounds thereof. Among the tachykinin antagonists derived from plants, substances having such an unexpectedly high activity are not known. The compounds of the present invention have an unexpectedly high tachykinin antagonistic activity and their source is an extract of *M. chamomilla* which is a quite frequently used plant for galenicals in Europe. Accordingly, their low toxicity and low side effects, and high safety make them highly useful as pharmaceuticals.

Tachykinins such substance P are neuro-peptides widely distributed in the living body and have been known to act in broad areas such as in diseases of the digestive system, nervous system and respiratory system. In particular, they strongly participate in inflammation, allergy, carcinoid syndrome, chronic pain, headache, Crohn disease, depression, vomiting, etc. Accordingly, a tachykinin antagonist is applicable to many diseases.

For example, as an anti-inflammatory agent, a tachykinin antagonist is useful for treatment of inflammation caused by asthma, influenza, adult respiratory distress syndrome (ARDS), chronic bronchitis, bronchospasm, chronic rheumatism, Crohn disease, ulcerative colitis, inflammatory intestinal disease, NSAID induced injury, blister, eczema, cystitis or incontinence, and inflammatory diseases of the eye or teeth.

A tachykinin antagonist is also useful for the treatment of an allergic disease such as asthma, skin allergic disease, urticaria, allergic respiratory disease, hypersensitivity to Rhus vemiciflua, rhinitis, atopic dermatitis, contact-type dermatitis, etc.

As an analgesic, it is useful for treatment of various pain diseases or conditions such as traumatic pain, postoperative pain, traumatic avulsion pain, brachial plexus pain, chronic pain, arthritic pain, herpetic neuralgia, arthrosteitis, chronic rheumatism, psoriatic arthritis, pain accompanied by nerve disease, post-herpetic neuralgia, burn-induced pain, intercostal neuralgia, opioid-resistant pain, causalgia, diabetic neuropathy, chemotherapy induced nerve disease, AIDS related nerve disease, occipital nerve disease, knee pain syndrome, glossopharyngeal nerve disease, sympathetic dystrophy, phantom limb pain, migraine, acute or chronic tension headache, temporomandibular pain, maxillary sinus pain, cluster headache, toothache, cancer pain, gastrointestinal pain, athletic disturbance pain, pain accompanied with parturition, menorrhalgia, pritonitis, arachnoiditis, musculoskeletal pain, low back pain, spinal stricture, urogenital pain such as cystitis, sciatica, anginal pain, ankylosing spondylitis, gout, burn, scar pain, thalamic pin, etc.

A tachykinin antagonist is useful as an antidepressant, antianxiety agent or antipsychotic for treatment of phychosis, schizophrenia, mania, dementia, cognitional disease, Alzheimer disease, anxiety, AIDS-related dementia, nerve degenerated disease such as Down syndrome, stroke, diabetic nerve disease, multiple sclerosis, depression, Parkinson disease, habitual disease such as alcoholism, drug- or substance-abuse and dependence, etc.

It is also useful for treatment of vomiting and therefore applicable to symptoms such as nausea, retching, sicchasia, acute vomiting, delayed or anaphase vomiting, or expectation vomiting. The pharmaceutical composition of the present invention is effective for vomiting induced by various causes, for example, vomiting as an adverse reaction caused by drugs such as a chemotherapeutic agent, alkylating agent, opioid analgesic, cytotoxic antibiotic and antimetabolic agent, vomiting accompanied by radiation disease caused by exposure to radiation, chest or abdominal radio-irradiation treatment or radiotherapy in cancer treatment, or vomiting caused by metabolic disease, infective disease, motor disease, vertigo, Meniere disease, postoperative disease, gastrointestinal obstruction, decreased gastrointestinal motility, visceralgia, conjunctivitis, migraine, change of intracranial pressure, dyspepsia, overeating, gastric hyperacidity, etc.

In addition, the present composition is effective for treatment of gastrointestinal disease such as irritable colon syndrome, dermal disease such as psoriasis, itching or sunburn, angioplastic disease such as angina, vascular headache or Raynaud disease, cerebral ischemic disease such as subarachnoid hemorrhage, or graft rejection, and autoimmune disease such as fibrosis, collagen disease, systemic lupus erythematosus or rheumatic disease.

A tachykinin antagonist in accordance with the present invention is also useful as a muscle relaxant or antispasmodic and is therefore effective for treatment of peripheral nervous disorder, stress related disease, sympathetic reflex dystrophy, shoulder-arm syndrome, dysthymic disorder and plasma transudation caused by cytokine chemotherapy.

As mentioned above, a substituted alkyltetraamine derivative of the present invention has an excellent tachykinin antagonistic activity and is, therefore, highly useful as a remedy for said various diseases.

We claim:

1. An isolated and/or purified compound which is represented by the following formula (I) or which is a pharmaceutically acceptable salt, a complex or a solvate of a compound represented by formula (I):

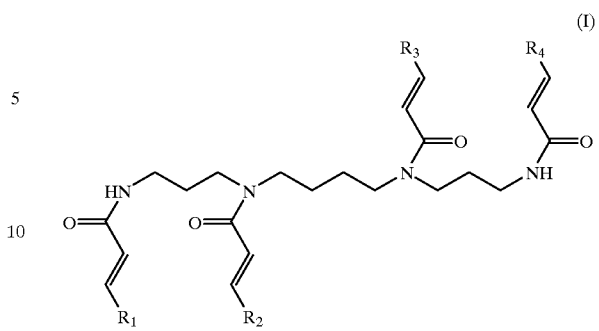

wherein $R_1$, $R_2$, $R_3$ and $R_4$ are the same or different and each of $R_1$, $R_2$, $R_3$ and $R_4$ is a phenyl group, or a phenyl group which is substituted with at least one member selected from the group consisting of hydroxyl, lower alkoxy and acyloxy groups.

2. A compound as claimed in claim 1 wherein each of $R_1$, $R_2$, $R_3$ and $R_4$ is a substituted phenyl group.

3. A compound as claimed in claim 1 wherein each of $R_1$, $R_2$, $R_3$ and $R_4$ is the same.

4. A compound as claimed in claim 1 wherein each of $R_1$, $R_2$, $R_3$ and $R_4$ is a phenyl group substituted with only one member selected from the group consisting of hydroxyl, lower alkoxy and acyloxy groups.

5. A compound as claimed in claim 1 wherein each of $R_1$, $R_2$, $R_3$ and $R_4$ is a hydroxyphenyl group.

6. A compound as claimed in claim 5 wherein said hydroxyphenyl group is a 4-hydroxyphenyl group.

7. A compound as claimed in claim 1 wherein each of $R_1$, $R_2$, $R_3$ and $R_4$ is a phenyl group substituted with two members selected from the group consisting of hydroxyl, lower alkoxy and acyloxy groups.

8. A compound as claimed in claim 1 wherein each of $R_1$, $R_2$, $R_3$ and $R_4$ is a phenyl group substituted with at least one hydroxyl group.

9. A compound as claimed in claim 1 wherein each of $R_1$, $R_2$, $R_3$ and $R_4$ is a phenyl group substituted with more than one hydroxyl group.

10. A compound as claimed in claim 1 wherein each of $R_1$, $R_2$, $R_3$ and $R_4$ is a phenyl group substituted with a methoxy group, a hydroxy group, an acetoxy group, or mixtures thereof.

11. A pharmaceutical composition comprising a pharmaceutically effective amount of a compound as claimed in claim 1.

12. A tachykinin antagonist composition comprising a pharmaceutically effective amount of a compound as claimed in claim 1 and a pharmaceutically acceptable carrier or diluent.

13. A pharmaceutical composition comprising a pharmaceutically effective amount of at least one compound as claimed in claim 1 which is isolated or purified from an extract of a plant belonging to the family Compositae.

14. A pharmaceutical composition as claimed in claim 13 wherein said plant is M. chamomilla.

15. A pharmaceutical composition as claimed in claim 14 wherein said at least one compound is N1,N5,N10,N14-tetrakis[3-(4-hydroxyphenyl)-2-propenoyl]tetraazatetradecane.

16. A method for the treatment of a tachykinin-related disease or condition comprising administering to a patient in need of such treatment a pharmaceutically effective amount of a tachykinin antagonist composition, said tachykinin antagonist composition comprising at least one compound as claimed in claim 1.

17. A method as claimed in claim 16 wherein said tachykinin-related disease or condition is selected from the group consisting of anxiety, depression, schizophrenia, senile pollakiuria, incontinence, Crohn disease, irritable colon syndrome, inflammatory intestinal disease, chronic articular rheumatism, vomiting, migraine, pain, ulcer, asthma, allergic diseases, ocular diseases, dermal diseases, other inflammatory diseases, and diabetic neuropathy.

18. A method as claimed in claim 16 wherein each of $R_1$, $R_2$, $R_3$ and $R_4$ is a phenyl group substituted with at least one hydroxyl group.

19. A method for producing a compound represented by the following formula (I) or a pharmaceutically acceptable salt, a complex or a solvate of a compound represented by formula (I):

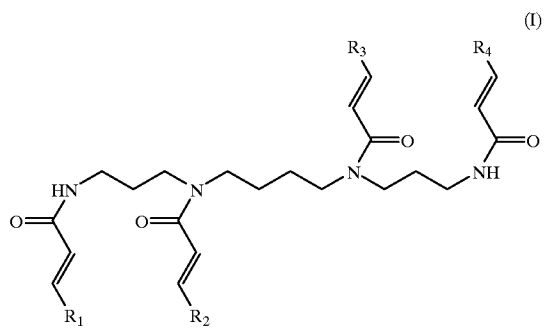
(I)

wherein $R_1$, $R_2$, $R_3$ and $R_4$ are the same or different and each of $R_1$, $R_2$, $R_3$ and $R_4$ is a phenyl group, or a phenyl group which is substituted with at least one member selected from the group consisting of hydroxyl, lower alkoxy and acyloxy groups comprising reacting spermine represented by the formula (II) or a reactive derivative thereof, with a carboxylic acid of formula (III) or a reactive derivative thereof:

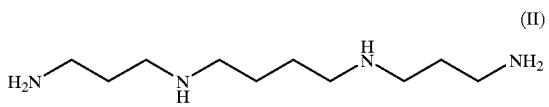
(II)

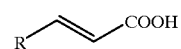
(III)

wherein R is a group corresponding to $R_1$, $R_2$, $R_3$ and $R_4$ in the formula (I).

20. A method as claimed in claim 19 wherein each of $R_1$, $R_2$, $R_3$ and $R_4$ is a phenyl group substituted with at least one hydroxyl group.

21. A method as claimed in claim 20, wherein the compound is N1,N5,N10,N14-tetrakis[3-(4-hydroxyphenyl)-2-propenoyl]tetraazatetradecane.

22. A compound which is represented by the following formula (I), or which is a pharmaceutically acceptable salt, a complex or a solvate of a compound represented by formula (I):

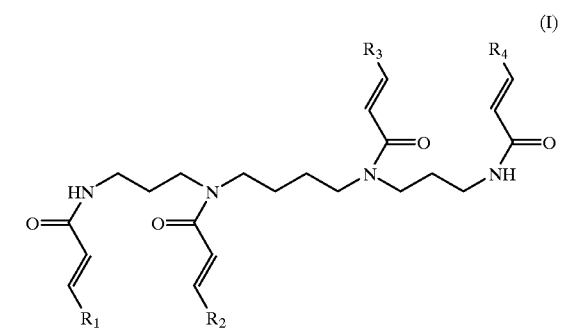
(I)

wherein $R_1$, $R_2$, $R_3$ and $R_4$ are the same or different and each is a phenyl group, or a phenyl group which is substituted with at least one member selected from the group consisting of hydroxyl, lower alkoxy and acyloxy, with the proviso that said compound is not N1,N5,N10,N14-tetrakis[3-(4-hydroxyphenyl)-2-propenoyl]tetraazatetradecane.

* * * * *